US006796164B2

(12) United States Patent
McLoughlin et al.

(10) Patent No.: US 6,796,164 B2
(45) Date of Patent: Sep. 28, 2004

(54) INTEGRATED FLUIDICS SYSTEM FOR SIMPLIFIED ANALYSIS OF AEROSOLIZED BIOLOGICAL PARTICLES AND PARTICLE DETECTION TICKET THEREOF

(75) Inventors: Michael P. McLoughlin, Sykesville, MD (US); Micah A. Carlson, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/288,128

(22) Filed: Nov. 4, 2002

(65) Prior Publication Data

US 2003/0087424 A1 May 8, 2003

Related U.S. Application Data

(60) Provisional application No. 60/332,788, filed on Nov. 6, 2001.

(51) Int. Cl.$^7$ ............................ G01N 1/00; G01N 37/00
(52) U.S. Cl. .................... 73/28.01; 73/28.02; 73/28.04; 73/28.05
(58) Field of Search .............................. 73/28.01, 28.02, 73/28.04, 28.05, 865.5

(56) References Cited

U.S. PATENT DOCUMENTS

| 3,998,734 A | * | 12/1976 | Barringer ..................... 210/808 |
| 6,520,034 B1 | * | 2/2003 | Masquelier et al. ..... 73/863.21 |
| 6,615,679 B1 | * | 9/2003 | Knollenberg et al. .... 73/863.33 |

FOREIGN PATENT DOCUMENTS

| EP | 1 067 199 A1 | 1/2001 |
| WO | 16714 | 5/1997 |

* cited by examiner

*Primary Examiner*—Daniel S. Larkin
(74) *Attorney, Agent, or Firm*—Francis A. Cooch

(57) ABSTRACT

An integrated fluidics system for simplified analysis of aerosolize biological particles has a unitary self-contained ticket provided with a sample fluid reservoir, an array of particle-detection strips, which is located adjacent to the sample reservoir, and, optionally, a cleaning fluid reservoir and an impinging nozzle. The fluidics system is, thus, configured to substantially minimize the fluid paths between the components of the system.

35 Claims, 4 Drawing Sheets

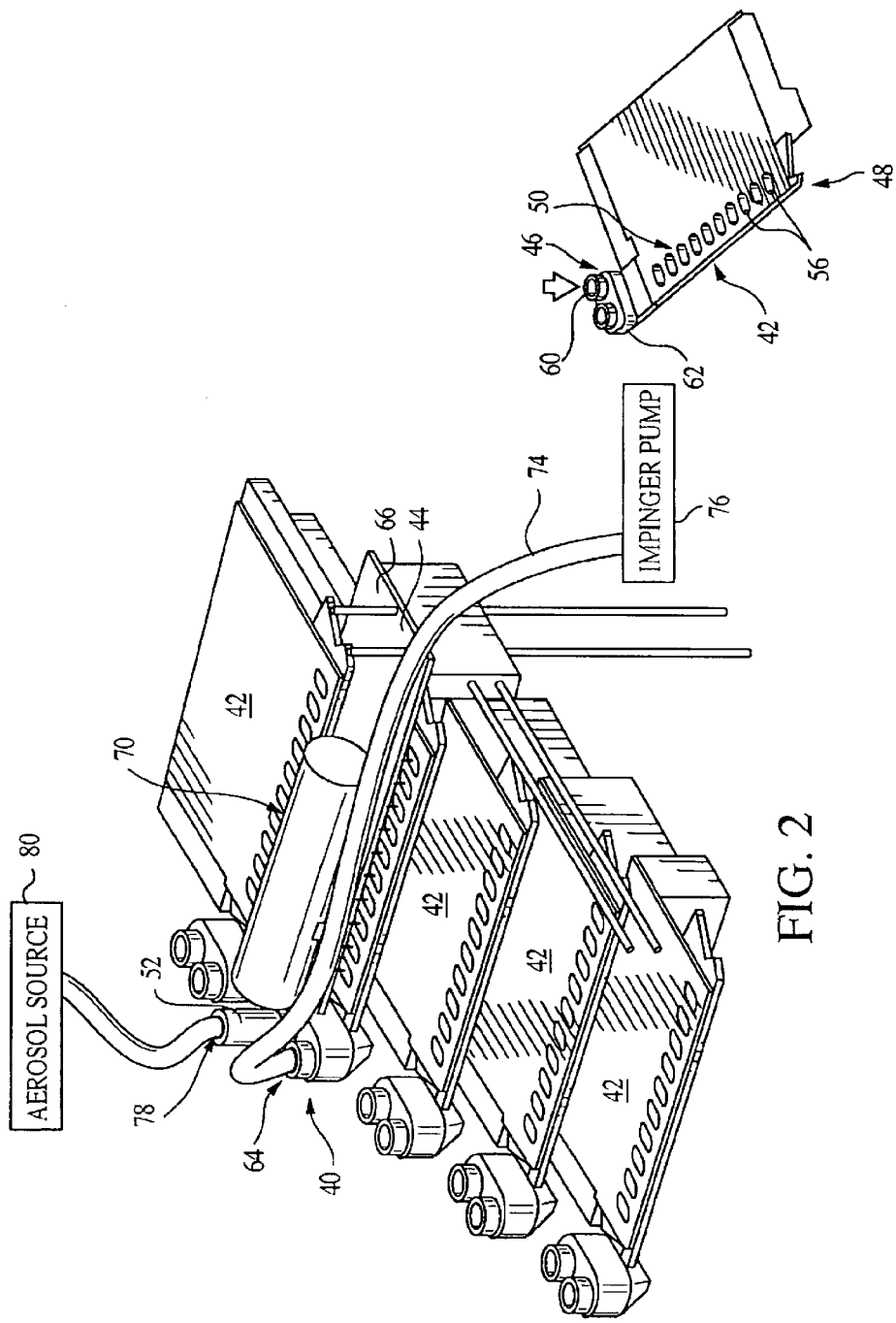

Figure 1:
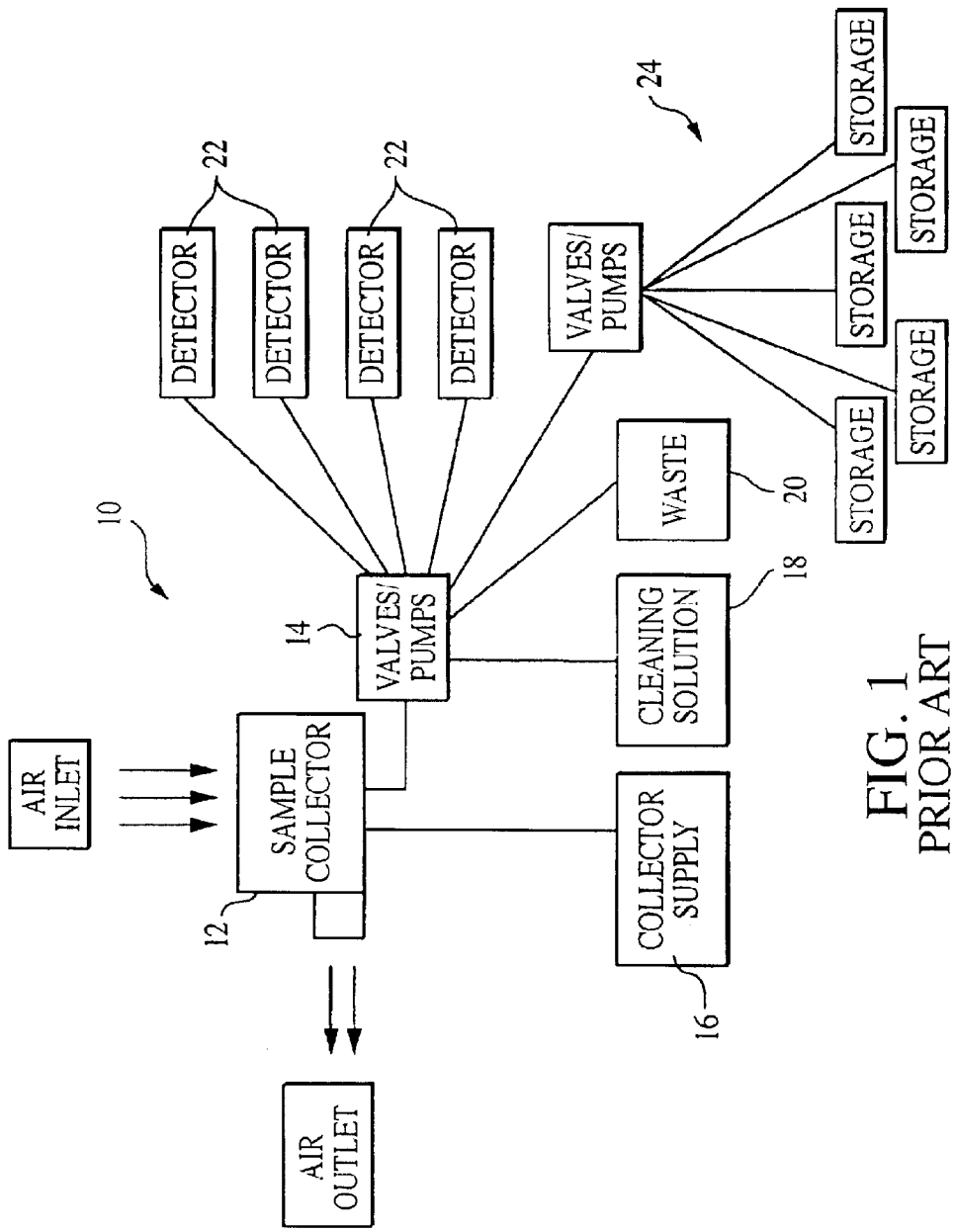
Figure 5:
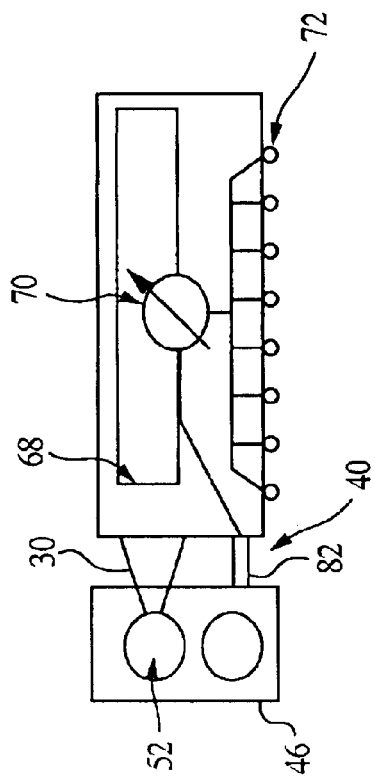
Figure 6:
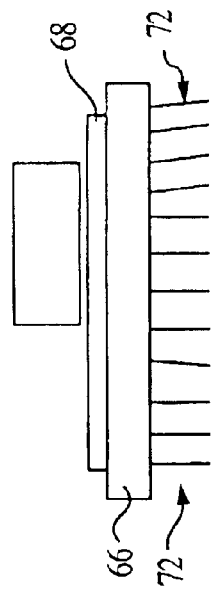
Figure 4:
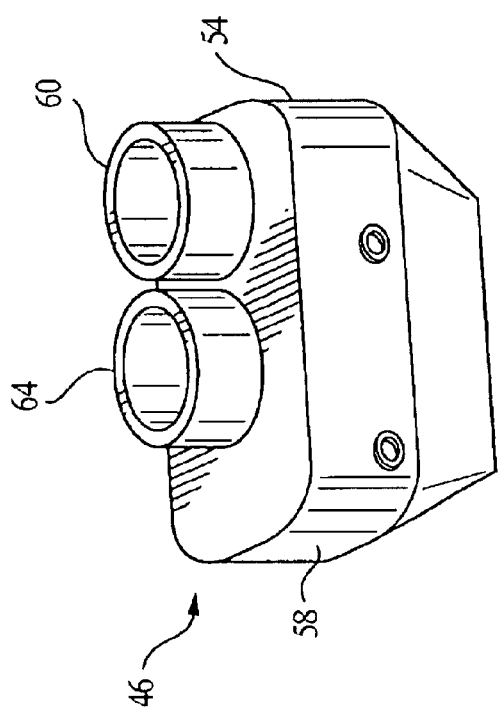

INTEGRATED FLUIDICS SYSTEM FOR SIMPLIFIED ANALYSIS OF AEROSOLIZED BIOLOGICAL PARTICLES AND PARTICLE DETECTION TICKET THEREOF

CROSS-REFERENCE TO RELATED APPLICATION

This application claims priority to U.S. Provisional Application Ser. No. 60/332,788 filed Nov. 6, 2001, the contents of which are incorporated by reference herein.

BACKGROUND OF THE INVENTION

1. Technical Field

This invention relates generally to diverse fields impacted by the nature of molecular interaction, including biology, chemistry, medicine and diagnostics. More particularly, this invention is directed to a miniaturized integrated system for analyzing airborne biological particles and microorganisms.

2. Description of Related Art

Obtaining accurate measurements of the particle and gas content in diverse environments including the earth's atmosphere is important for monitoring and understanding such environments. Detection of biological warfare agents, collection of industrial pollutants in ambient air and fluids and sampling the same, collection of infectious or disease-causing organisms in closed and open spaces, as well as collection of radioactive particles or toxic vapors are just a few examples illustrating application of a system for analyzing biological particles and microorganisms.

The detection of low concentrations of aerosolized particles, i.e., particles suspended in air, generally requires that the particles be extracted from a large volume of air in order to capture a sufficient number of particles to exceed a detection threshold of a detection technique. For example, it is not uncommon to require the detection of aerosol concentrations of less than one hundred particles per liter of air. Typically immunoassay-type systems require approximately 100,000 organisms to achieve a successful detection. Obtaining this result from low concentrations can require particle extraction from over 1500 liters of air. Completion of this task in a timely manner (several minutes) requires that large volumes of air be processed.

Much effort has been expended in the past in the detection and classification of particles or aerosols in fluid streams. Impactors have been used for collecting aerosol particles for many decades. In the earliest embodiments, a stream of fluid containing the particles was accelerated toward an impactor plate. Due to their inertia, the particles hit the impactor plate and were collected there while the fluid was deflected to the side. With these types of impactors, only heavy particles were collected while particles below a certain "cut size" were carried away by the fluid stream.

However, a significant cause of inaccuracy in such impactors results from the deposition of particles on surfaces of the impactor other than the intended collection surfaces. This phenomenon reduces the accuracy of measurement of total particle mass concentration and of the size-fractionation of particles, since such losses cannot be accurately estimated for aerosols having varying size, shape, or chemistry. Additionally, particles may either reenter the fluid stream or bounce from the impactor's collection surface upon impact.

Another method for the detection and classification of particles is based on removing aerosolized particles from fluid streams by centrifugal force. This method is usually referred to as a "cyclone." In accordance with this method, the aerosol is drawn into a cylindrical chamber so that the air makes one or more rotations inside before leaving the chamber through a tube at its center. Particles with sufficient inertia move centrifugally toward the inner wall.

A detection system associated with the cyclone principle of operation collects airborne particles from large volumes of air and concentrates the collected particles in a small volume of fluid. This fluid then can be inserted into a detection device such as an immunoassay cartridge to determine if a specific biological organism or agent is present. A schematic of such a system is shown in FIG. 1.

In the shown system, air is drawn into a liquid-impinging system 10 such as a wetted wall cyclone or other sample collector 12. As the air moves in a circular path, the water level rises, and particles impacting upon the surface of the sample collector 12 are captured in the fluid while the particle-free air exists out via the top of the jar. The fluid with captured particles is further transported for analysis by means of valves or pumps 14. Systems intended to detect harmful biological agents require the delivery of the sample fluid to an array of immunoassay cartridges so that multiple analyses may be performed. Typically, the sample collector provided with an impinger nozzle is located a substantial distance from a multiplicity of tickets, each of which typically carries only an array of immunoassay strips. To couple the collector 12 with the selected ticket, the latter is moved to a location to be connected to the collector 12 via a pump 14 and a system of valves providing sample flow into the strips of the connected ticket. Once the strips are filled, the ticket is again displaced a substantial distance toward a detector 22, which is configured to detect harmful agents. Upon completion of a positive detection, the remaining contents of the sample collector 12, if any, are drained. A large volume cleaning solution reservoir 18 is then coupled to the collector 12 and to the sample-solution conveying parts, such as, for example, the fluid transfer pump and coupling lines, to clean and prepare them for a subsequent test; once the cleaning stage is completed, the contaminated solution is accumulated in a large-volume waste basin 20.

Thus, the present technology requires that fluid from a single collection be transported a long distance to the detector. Before a new sample can be collected, analysis of the previous sample must be completed and the fluidics cleaned to prevent cross contamination. This process limits the maximum rate at which samples can be processed and amounts to a process that lasts about fifteen minutes.

Only after minimizing the possibility of cross-contamination, a new volume of the liquid is supplied from a collector supply 16 into the sample collector 12 to provide a trap for a new portion of particles entering the collector along with incoming air stream. To preserve tested samples for further consideration, a multiplicity of storage reservoirs 24 can be filled upon the completion of each test.

Thus, to summarize above, there are several significant disadvantages to this approach. First, transfer of the collected fluid to the detector is very complicated for multiple use systems. Second, between each analysis cycle the system must be purged to reduce cross contamination, requiring additional time and consumables. Third, the long fluid paths and complicated valve systems increase the likelihood of the system clogging due to environmental contaminants. Finally, in cold weather, significant power is required to prevent the fluids in the system from freezing.

It is, therefore, desirable to provide a simplified system for detecting aerosolized biological particles that requires fewer fluid-containing and fluid-conveying components and minimizes efforts directed to coupling these components for conducting a multiplicity of sequential tests.

SUMMARY OF THE INVENTION

To attain this, the present invention provides for a new configuration of a particle or sample collection and detection component, further referred to as a ticket, which includes, in addition to a cartridge provided with a row of immunoassay strips, a combination of an impinging nozzle, and sample reservoir. Optionally, a cleaning solution storage or reservoir can be an integral part of the inventive ticket. Thus, the inventive ticket is an integrated structural unit including a sample capturing and accumulating system, a cleaning system and a detecting system.

One of the advantages of the inventive ticket is the minimization of all fluid paths. Indeed, placement of a sample reservoir practically adjacent to a row of strips substantially reduces the distance which the sample solution travels between these components. Furthermore, by optionally providing each individual ticket with cleaning fluid or a solution reservoir, the system eliminates long cleaning-solution paths and obviates the need for a large-volume single cleaning fluid reservoir as well as for a waste basin. In the inventive system, as a testing stage is completed, the cleaning fluid is pumped out from the cleaning fluid reservoir to those fluid conveying parts which are not located on the ticket, and after the cleaning stage is complete, the contaminated solution returns back into the same reservoir. Note that upon completion of the test, the ticket, most likely, will not be needed.

Thus, having reduced the distance fluid travels and the number of components, the inventive fluidics system is simple and both space- and cost-efficient.

In accordance with a further aspect of the invention, the inventive system features a sample detection and fluid distribution component or unit detachably connectable to each of the tickets to provide controllable delivery and detection of agents and, also, delivery of cleaning solution or fluid after the detection test has been completed. The sample detection component includes a fluid transfer pump, a sample detector, solution and sample conveying elements as well as an air conduit to draw an air stream into the sample reservoir formed on the ticket.

Accordingly, the inventive system is a compact sample detection stage or system including two separate inventive units detachably coupled to one another. One of the units—the ticket—has sample collecting reservoir and multiple immunoassay strips, and the other unit—the sample detection and fluid distribution component—has a means for distributing and detecting the sample.

Overall, the provision of the sample detection and fluid distribution component allows the user to provide a sequence of tests in a time-efficient manner substantially improving the known methodology of and the system for analyzing biological particles and microorganisms. The inventive system, in which the sample fluid reservoir and optionally the impinging nozzle and the cleaning solution reservoir are formed as a unit and attached to a cartridge provided with the immunoassay strips substantially minimizes the length of solution paths and simplifies the overall structure.

OBJECTS OF THE INVENTION

It is, therefore, an object of the invention to provide an integrated fluidics system for simplified analysis of aerosolized biological particles overcoming drawbacks of the known prior art systems.

A further object of the invention is to provide a self-contained sample or particle collection component or ticket having integrated therein a sample fluid reservoir.

Yet another aspect of the invention is to provide a sample detection and solution-distribution unit removably attachable to the ticket and providing the overall system with miniaturized fluidics contributing to a smooth and efficient process for conducting multiple tests.

Another object of the invention is to provide a controllable integrated sampling stage substantially minimizing mechanical operations.

Yet a further object of the invention is to provide a new and efficient method of controlling the integrated sampling stage.

BRIEF DESCRIPTION OF THE DRAWINGS

The above and other objects, features and advantages will become more readily apparent from the following detailed description of the invention accompanied by the drawings, in which:

FIG. 1 is a general diagrammatic view of a sampling stage of the prior art detection systems;

FIG. 2 is an isometric view of an integrated fluidics sampling system configured in accordance with the invention;

FIG. 3 is an isometric view of a particle collection and detection component or ticket of the inventive system, as shown in FIG. 2;

FIG. 4 is an isometric view of a collection and storing assembly of the ticket, as illustrated in FIG. 3;

FIG. 5 is a diagrammatic top view of the inventive sampling system, as shown in FIG. 2;

FIG. 6 is a diagrammatic front view of the inventive sampling system; and

FIG. 7 is a diagrammatic view of the inventive system diagrammatically showing a control system for operating the inventive system in a control mode.

DESCRIPTION OF THE PREFERRED EMBODIMENTS

To simplify the fluidics of the prior art system illustrated in FIG. 1, the invention, as better seen in FIG. 2, provides for an integrated fluidics system or stage 40 (FIG. 3) having a particle collecting unit or a ticket 42 and a sample detection and fluid-distribution unit 44. Both units are detachably matable with one another to provide a simple, compact structure of the integrated sampling stage characterized by fewer components and short fluid lines between individual components of each of the units as well as therebetween.

Referring to FIGS. 3–4, in accordance with one aspect of the invention, the ticket 42 is configured to have a particle collection/storage component 46 and a particle detection component 48 integrated in a singular rigid structure. Structurally, the ticket 42 has a housing 62 providing a rigid and reliable support for the particle collection/storage unit 46, which includes an inlet port 60 traversed by air stream carrying the particles to be tested and a sample fluid reservoir 54. Optionally, the ticket 42 can be provided with a cleaning fluid reservoir 58. Both sample fluid 54 and cleaning fluid 58 reservoirs are separate compartments formed in the housing of the collection/storage unit 46. Collocated with the unit 46 is a cartridge 50 carrying an array of immunoassay strips 56 which form the detection component 48 and receive sample fluid with captured particles therein from the sample fluid reservoir 54 in a manner as will be explained herein below.

Functionally, the strips 56 are provided with a reactant capable of producing a reaction with agents to be detected which may be accompanied by a color change, heat or any other effect detectable by a variety of techniques such as a camera-based system, a chip-based technology and the like. Regardless of the nature of the reaction, the latter is intended to indicate the presence of the agents in the tested sample delivered to the strips 56 from the sample fluid reservoir 54.

While the locations of the ticket components can be arranged in a variety of ways as long as all of them are collocated on the unitary structure, providing the housing 62 with the sample fluid reservoir 54 on one of the opposite ends of the elongated cartridge is preferred. In this configuration, the spaced strips 56 extend along the longitudinal direction of the cartridge 50 between its opposite ends. Also note that the housing 62 with at least the fluid sample reservoir and the cartridge 50 carrying the immunoassay strips can be detachably coupled so that any combination of elements of the overall system can be assembled in accordance with given requirements.

To provide a steady aerosol flow into the collection/storage unit 46, the housing 62 encloses at least one compartment, which defines the sample fluid 54 reservoir, and carries the air inlet port 60 and an air exhaust port 64 which project from the housing 62. The air inlet port 60 provides flow communication between an aerosol source, which can be an ambient environment or an air-to-air concentrator 80 (FIG. 2), such as the Army's XM2 and MesoSystems Technologies micro VIC utilizing virtual impaction to concentrate particles into lower flow streams. As the incoming air stream enters the inlet port 60, the particles accelerate and impact into a sample fluid, which, thus, captures the particles in the sample fluid reservoir 54.

To accelerate the particles, the invention provides for an impinging nozzle configured so that the particles while being guided along the surface of the nozzle 52, (only schematically shown in FIGS. 2 and 5), increase their speed. While the impinging nozzle may be mounted on the ticket 42 or on a sample detection and fluid-distribution unit 44 (FIG. 2), as will be discussed below, it must be in flow communication with the air inlet port 60.

As the particles are being captured by sample fluid, the "clean" air stream flowing along an air path exits the housing 62 through the air exhaust port 64 (FIGS. 2 and 4) for reasons that will be explained herein below. As the particles trapped in the sample fluid reservoir reach a desired concentration, incoming airflow ceases and the sample fluid is ready to be transported in to the adjacent particle detection component 48 and distributed among the immunoassay strips 56.

The compulsory guidance of the aerosol into the ticket 42, evacuation of the "clean" airflow therefrom and transportation of the sample fluid with the trapped particles to the strips 56 is provided by the sample detection and fluid-distribution unit 44 (FIG. 2) configured in accordance with another aspect of the invention.

Referring to FIGS. 2, 5 and 6, the unit 44 includes a platform 66 dimensioned to coextend with the array of the immunoassay strips 56 during a test. The platform 66 is rather flat to be able either placed atop the ticket 42 or to be juxtaposed therewith at an insignificant distance. Detachably mounted on the platform is a fluid transfer pump 70 operative to draw the sample fluid from the sample fluid reservoir 54 and deliver it to the strips 56. Distribution of the sample fluid among the strips 56 is fulfilled by a number of injecting nozzles 72 extending from the platform and being in flow communication with sample-fluid conveying parts extending between the transfer pump 70 and the injecting nozzles 72. A sensor 68 operative to detect the presence of the particles or agents of interest is located under the transfer pump 70 so that, during the test, it opposes the array of strips 56. Advantageously, the sensor 68 is a CCD camera capable of detecting a color change. Alternatively, an operator can read the strips.

Other types of sensors operative to detect heat radiation or any other reaction-indicative effects can be easily implemented within the scope of this invention. Depending on a size of the inventive integrated fluidics system 40, the number of the strips 56 and on other local requirements, either one or a multiplicity of CCD cameras are envisioned within the scope of the invention. Finally, the platform 66 is provided with an exhaust air-conveying conduit 74 intended to be in flow communication with the exhaust port 64 during the test.

To conduct the test, the opposite ends of the exhaust air-conveying conduit 74 are connected to the air exhaust port 64 and an impinger pump 76 (FIG. 2), respectively, and an inlet air conduit 78 conveying an air stream is attached to the impinging nozzle 52 detachably sealed to the inlet port 60. To provide a flow path of the sample and cleaning fluids between the ticket 42 and the unit 44, the system 40 (FIG. 5) has a fluid conveying conduit, such as a needle 82 selectively providing flow communication between the transfer pump 70 and the sample fluid 54 and cleaning fluid 58 reservoirs.

In operation, the ticket 42 and the sample detection and fluid-distribution unit 44 of the integrated fluidics system 40 are positioned relative one another so that the CCD camera 68 opposes the strips 56. After the preparation stage, as discussed above, the impinger pump 76 is operative to create a slight vacuum on the impinger volume that contains the sample fluid to draw aerosol with particles to be tested through the air inlet 60. While the particles accelerate along the surface of the impinger nozzle 52 and are captured in the sample fluid, the airflow continues to flow along the conduit 74. In the embodiment, as shown in FIG. 5, the unit 44 has a rigid support 30 carrying the impinging nozzle 52 detachably coupled therewith. However, it is also contemplated that the impinging nozzle 52 can also be mounted on the ticket. Regardless of the position of the impinging nozzle, once the sample fluid has become sufficiently concentrated, the transfer pump 70 is turned on to transfer and distribute the sample liquid through the sample needle 82 and further via the injecting nozzles 72 into the strips 56. Following the analysis conducted by the CCD camera 68, the sample needle 82 is switched to be in flow communication with the cleaning fluid reservoir 58 located either in the ticket 42 or outside thereof. Thus, when the transfer pump 70 is attached to the cleaning fluid reservoir 58, cleaning fluid is pumped along the sample needle 82, the impinging and injecting nozzles 72 and other fluid conveying parts of the unit 44 to minimize the risk of cross-contamination. Following the cleaning stage, the transfer pump reverses the pumping direction to evacuate the contaminated cleaning fluid back to the cleaning fluid reservoir 58. Once the fluid conveying components located on the unit 44 are free from contaminants and ready to be coupled to a next ticket, the previous ticket with the collocated sample and the contaminated cleaning fluid reservoir is simply discarded, or retained for future analysis using a variety of techniques.

Thus, the inventive system simplifies the fluidics by collocating the sample and cleaning fluid reservoirs on the single support structure of the ticket. As a result, sample fluid is pumped directly to the assay strip cartridge 50, thus eliminating the long fluid paths associated with prior art bio-detection systems. Accordingly, the inventive system is characterized by an increased sample rate due to the elimination of the need to transport fluids between the collector, the detector, and the same sample containers. Furthermore, because of the inventive combination of the ticket and the sample detection and fluid-distribution unit, there is no need to clean sample collectors as well as to have large-diameter fluid reservoirs driving complexity and cost of the known systems high.

While the embodiment as shown above uses an immunoassay cartridge, the approach is equally applicable to other biological analysis technologies such as Polymerase Chain Reaction (PCR), mass spectrometry, Gene Chips, ELISA, and other analytical methods.

Figure 7:
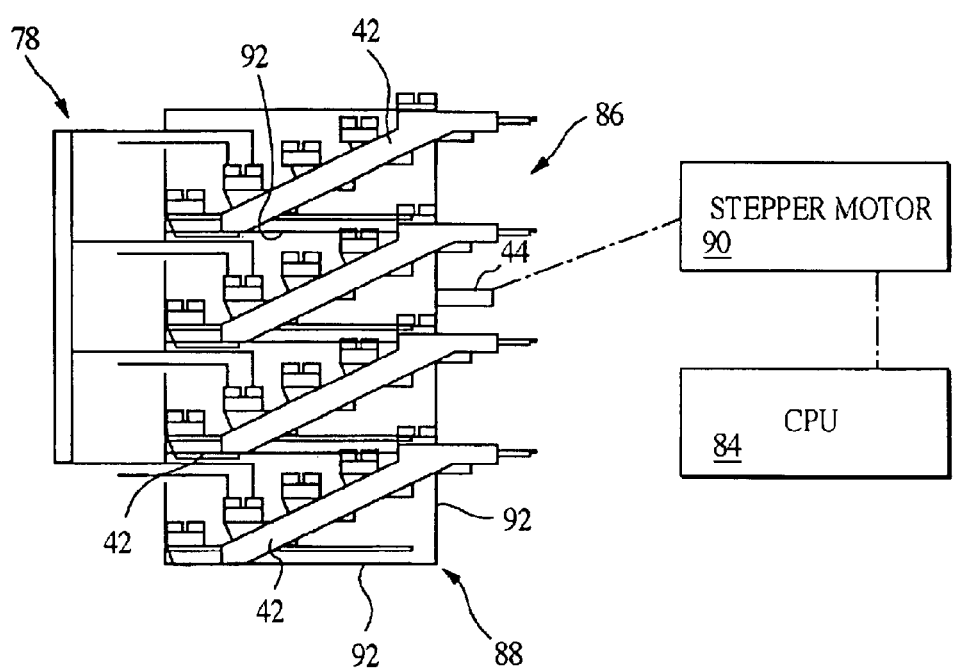

Referring to FIG. 7, in accordance with yet another aspect of the invention, the inventive system may be used in an automatic mode. As shown, a stack of multiple magazines 86 each having a plurality of tickets 42 can be associated with a track and guide system 88 for automatically displacing the sample detection and fluid-distribution unit 44 both between the magazines and between the tickets of the same magazine. Controllable displacement is managed by a central processing unit (CPU) 84 having software for operating a stepper motor 90 coupled to the unit 44 so that the latter moves precisely between subsequent destinations along a plurality of guides 92 of the guide system 88. As the unit 44 reaches a desired position, software executed by the CPU 84 is operative to automatically connect the impinging nozzle 52, the sample needle 82 and the air exhaust conduit 74 with the inlet 60 and exhaust 64 ports and the sample fluid reservoir 54 on the ticket 42. The CPU 84 is further operative to automatically turn on the exhaust 76 and transfer 70 pumps to provide the entry of aerosol and subsequently to provide flow communication between the sample fluid reservoir 54 and the assay strips 56. Finally, the CPU 84 is operative to switch a fluid path to provide flow communication between the cleaning fluid reservoir 58 and the coupled platform in a time-controllable manner. By controlling a pumping rate and/or time of pumping of the transfer pump 70, the system can efficiently fill the sample fluid reservoir 54 and conduct the test. Upon completion of the test, software executed by the CPU 84 is operative to displace the unit 44 toward a next desired ticket.

Depending on the configuration of the magazines, it is envisioned to displace the tickets 42 or the individual magazines 86 relative to the sample detection and fluid-distribution unit 44. Furthermore, relative displacement of the magazine 86 and the unit 44 is envisioned as well. Using the architecture presented in FIG. 7, it is possible to immediately start a new collection after completion of the previous collection and to reduce the cycle time to two minutes from approximately eighteen minutes necessary for completion of a cycle by the prior art systems dependent on the analysis technique used. While real time analysis is the main objective of the inventive system, the above-described control system can provide a post-analysis mode of operation when it is desirable to confirm the results of the previous tests. The CPU 84 is operative to guide the unit 44 and the tickets 42 relative to one another so that in response to a desired location inputted by the user, the unit 44 may be juxtaposed with the desired ticket for a secondary test. Note that a manual mode, in which the unit 44 is manually guided to the desired location, at which all valve and conduit attachment operations are performed manually, is envisioned as well.

Also, it is envisioned to provide flow of sample fluid from the ticket 42 and to the fluid distribution unit 44 in addition to the system featuring the transfer pump, with a system that may create a positive pressure in the sample fluid reservoir. Alternatively, the entire system may work under gravity, wherein the fluid distribution unit 44 and the ticket 42 are so positioned relative to one another that fluids from all the reservoirs flow under gravity to desirable destinations. Such a relative positioning may be achieved either automatically or manually.

Thus, this invention provides for a new configuration of a particle or sample collection module, such as the housing enclosing at least the sample fluid reservoir, coupled directly to a detection system such as the array of immunoassay detection strips that test the fluid for a variety of agents. The strips can be automatically read by a sensor such as an integral or remote CCD that makes up part of the single detection unit or component, or manually read by a human operator. In addition to the sample fluid reservoir, the sample collection module can have a single or multiple impinging nozzles that effectively place airborne particles into the sample fluid reservoir. A sample from the fluid reservoir is then moved to the immunoassay strips via a pressurized, vacuum, or gravity fed fluidics handling system. Thus, the inventive system features the ticket and the fluid distribution component or unit detachably connectable to each other to provide controllable delivery and detection of agents.

The invention is not limited to the disclosed preferred embodiment, and should be construed to cover all such alternatives, modifications and equivalents as defined in the appended claims.

What is claimed is:

1. A self-contained particle-detection ticket comprising an inlet port traversed by an incoming air stream carrying airborne particles to be tested, and a sample fluid reservoir in flow communication with the inlet port, the sample fluid reservoir storing sample fluid capturing the airborne particles as the air stream flows along an air path and in flow communication with a particle-detection sensor for detecting the airborne particles contained in the sample fluid.

2. The ticket of claim 1, the particle-detection sensor comprising an array of immunoassay strips receiving the sample fluid with the captured airborne particles to provide a reaction, if particles to be detected are present in the sample fluid, the inlet port being in flow communication with and downstream from an impinging nozzle traversed by the air stream, the sample fluid reservoir and the array of immunoassay strips are located adjacent to one another and are supported by a unitary cartridge, the ticket further comprising an exhaust port in flow communication with the inlet port for providing exhaust flow of the air stream substantially free from the particles.

3. The ticket of claim 2, further comprising an inlet air conduit in flow communication with an air-to-air concentrator providing the air stream and with the impinging nozzle, and an exhaust air conduit providing communication between an impinger pump and the exhaust port, the impinger pump being operative to create a vacuum sufficient to draw the air stream into the inlet port.

4. The ticket of claim 2, wherein the impinging nozzle is configured to provide acceleration of the airborne particles so that the accelerated airborne particles impact into the sample fluid and remain captured therein.

5. The ticket of claim 2, wherein the array of immunoassay strips and the sample fluid reservoir are in flow communication with one another generated by a transfer pump detachably coupled to the sample fluid reservoir.

6. The ticket of claim 3, wherein the sample fluid, the inlet, and exhaust ports constitute a unit fixed to the unitary cartridge.

7. The ticket of claim 5 further comprising a cleaning fluid reservoir flow-isolated from the sample fluid reservoir and in flow communication with the transfer pump, the cleaning fluid reservoir being provided either within the unitary cartridge adjacent to the sample fluid reservoir or separately from the unitary cartridge.

8. The ticket of claim 7, wherein the unitary cartridge further supports a sample/cleaning fluid conveying conduit selectively coupling the transfer pump with the sample fluid reservoir and the cleaning fluid reservoir.

9. The ticket of claim 5, wherein the array of the immunoassay strips and the transfer pump are in flow communication with one another via a plurality of injecting nozzles in flow communication with the transfer pump; and filling the immunoassay strips with the sample fluid to provide a reaction detected by a sample detector, if the particles to be detected are present in the sample fluid.

10. The ticket of claim 7, wherein the transfer pump is in flow communication with the cleaning fluid reservoir upon completion of a test and operates to guide cleaning fluid through the sample/cleaning conveying conduit to the injecting nozzles and back into the cleaning fluid reservoir.

11. An integrated fluidics system for analysis of aerosolized biological particles, comprising:
at least one self-contained ticket formed with a cleaning fluid reservoir and an array of particle-detection strips located adjacent to the reservoirs; and
a sample detection and fluid-distribution unit detachably coupled to the at least one self-contained ticket to provide flow communication between the array of particle-detection strips and a sample fluid reservoir.

12. The fluidics system of claim 11, further comprising an impinging nozzle located between the at least one self-contained ticket and the sample detection and fluid-distribution unit and configured to accelerate airborne particles contained in an air stream traversing the impinging nozzle so that the accelerated airborne particles impact into sample fluid stored in the sample fluid reservoir and are captured therein.

13. The fluidics system of claim 12, wherein the at least one self-contained ticket has a housing provided with the sample fluid reservoir, the fluidics system further comprising a sample fluid reservoir flow isolated from the sample fluid reservoir and from the array of detection strips, the housing being provided with an inlet port downstream from the impinging nozzle and in flow communication therewith and with an outlet port in flow communication with the inlet port and guiding the air stream substantially free from the airborne particles from the housing.

14. The fluidics system of claim 13, wherein the cleaning fluid reservoir is provided within the housing as an integral part of the ticket or separately from and at a distance from the housing.

15. The fluidics system of claim 12, wherein the sample detection and fluid-distribution unit includes a platform carrying the impinging nozzle, and a transfer pump in flow communication with the sample fluid reservoir for controllably transporting the sample fluid toward the array of the particle-detection strips.

16. The fluidics system of claim 15, wherein the detection and fluid-distribution unit has a series of injecting nozzles supported on the platform and in flow communication with the transfer pump, whereas the injecting nozzles distribute the sample fluid delivered by the transfer pump among the particle-detection strips.

17. The fluidics system of claim 15, wherein the platform of the sample detection and fluid-distribution unit supports a CCD camera opposing the array of the particle-detection strips and operative to detect a reaction if the particles to be detected are contained in the sample fluid.

18. The fluidics system of claim 15, wherein the sample detection and fluid-distribution unit further has a sample/cleaning fluid-conveying conduit controllably coupled to the sample and cleaning fluid reservoirs to selectively provide fluid flow between the transfer pump and the sample and cleaning fluid reservoirs.

19. The fluidics system of claim 18, further comprising a valve assembly in flow communication with the sample/cleaning fluid conveying conduit and with the transfer pump and operative to controllably couple the conduit with the sample and cleaning fluid reservoirs.

20. The fluidics system of claim 19, wherein the transfer pump is operative to provide fluid flow from the cleaning fluid reservoir through the fluid-conveying conduit into injecting nozzles to decontaminate the injecting nozzles, and to reverse the fluid flow upon completion of decontamination to direct contaminated fluid back into the cleaning fluid reservoir.

21. The fluidics system of claim 13, further comprising an impinger pump in flow communication with the outlet port for creating a vacuum in the inlet port sufficient to draw inflow of the air stream carrying the airborne particles.

22. The fluidics system of claim 21, further comprising an air-conveying conduit coupling the impinger pump and the outlet port and located on a platform of the sample detection and fluid-distribution unit.

23. The fluidics system of claim 11, further comprising another self-contained particle-detection ticket attached to the at least one self-contained particle-detection ticket, and a guide system configured so that the sample detection and fluid-distribution unit and each of the self-contained particle-detection tickets are displaceable relative to one another to provide intercoupling in a controllable manner.

24. The fluidics system of claim 23, further comprising a central processing unit having software operative to actuate a stepper motor coupled to and displacing the sample detection and fluid-distribution unit provided with a transfer pump and each of the at least one and other self-contained tickets relative to one another.

25. The fluidics system of claim 24, wherein the central processing unit further has software operative to actuate the transfer pump so that the sample fluid is pumped at a controlled rate and/or for a controlled period of time.

26. The fluidics system of claim 19, wherein a central processing unit has software operative to controllably switch the valve assembly to provide selective fluid communication between the transfer pump and the sample and cleaning fluid reservoirs.

27. The fluidics system of claim 24, wherein the central processing unit has software operative to controllably displace the sample detection and fluid-distribution unit among a plurality of magazines each containing the at least one and other self-contained tickets and among the at least one and the other self-contained tickets of each of the magazines.

28. A sample detection and fluid-distribution unit for use in a particle detection and analysis system comprising a platform supporting a fluid transfer pump, a plurality of injecting nozzles in flow communication with the transfer pump and a particle-detection sensor for detecting low concentration particles contained in sample fluid delivered by the transfer pump through the injecting nozzles.

29. The unit of claim 28, wherein the platform further has a sample/cleaning fluid conveying conduit providing flow communication between a sample fluid reservoir storing the sample fluid and the injecting nozzles, the sample fluid reservoir being provided in a self-contained particle-detection ticket detachably coupled to the sample/cleaning fluid conveying conduit.

30. The unit of claim 29, wherein the transfer pump is operative to deliver cleaning fluid through the sample/cleaning fluid conveying conduit from a cleaning fluid reservoir into the injecting nozzles to decontaminate the injecting nozzles, the cleaning fluid reservoir being provided in the self-contained particle-detection ticket adjacent to and in flow isolation with the sample fluid reservoir.

31. The unit of claim 30, wherein the sample fluid is transferred by the transfer pump and distributed via the injecting nozzles among a plurality of immunoassay strips located on the self-contained particle detection ticket adjacent the sample and cleaning fluid reservoirs.

32. An integrated fluidics system for analysis of agents, comprising a housing provided with a sample fluid reservoir, a detection unit, and a fluid-distribution unit detachably coupled to one another to assemble a one-piece assembly and to provide controllable delivery and detection of agents carried by a sample fluid within the one-piece assembly.

33. The integrated fluidics system of claim 32, wherein the housing further includes at least one inlet port receiving an air stream with the agents to be detected.

34. The integrated fluidics system of claim 32, wherein the detection unit includes a cartridge carrying a plurality of immunoassay strips.

35. The integrated fluidics system of claim 32, wherein the fluid-distribution unit includes means for creating negative or positive pressure in the housing to deliver the sample fluid to the detection unit.

* * * * *